US012780760B2

(12) United States Patent
Balasanthiran et al.

(10) Patent No.: US 12,780,760 B2
(45) Date of Patent: Nov. 3, 2026

(54) MONOALKYL CYCLOPENTADIENE COMPOUNDS AND PROCESSES FOR PREPARING SAME

(71) Applicant: ENTEGRIS, INC., Billerica, MA (US)

(72) Inventors: Vagulejan Balasanthiran, Pennsburg, PA (US); Scott A. Laneman, Vernon Hills, IL (US); Jon Alkema, Abington, PA (US); Thomas Kermis, Lansdale, PA (US)

(73) Assignee: Entegris, Inc., Billerica, MA (US)

( * ) Notice: Subject to any disclaimer, the term of this patent is extended or adjusted under 35 U.S.C. 154(b) by 547 days.

(21) Appl. No.: 18/530,015

(22) Filed: Dec. 5, 2023

(65) Prior Publication Data

US 2024/0116836 A1 Apr. 11, 2024

Related U.S. Application Data

(62) Division of application No. 17/988,544, filed on Nov. 16, 2022, now Pat. No. 11,884,606.

(60) Provisional application No. 63/283,855, filed on Nov. 29, 2021.

(51) Int. Cl.

| | |
|---|---|
| ***C07C 1/32*** | (2006.01) |
| ***C07C 2/86*** | (2006.01) |
| ***C07C 13/15*** | (2006.01) |
| ***C07F 7/08*** | (2006.01) |
| ***C07F 17/00*** | (2006.01) |

(52) U.S. Cl.

CPC .............. *C07C 1/326* (2013.01); *C07C 2/867* (2013.01); *C07C 13/15* (2013.01); *C07F 7/0805* (2013.01); *C07F 7/0827* (2013.01); *C07C 2601/10* (2017.05); *C07F 17/00* (2013.01)

(58) Field of Classification Search

CPC ......... C07C 13/15; C07C 2/867; C07C 1/326; C07F 7/0805; C07F 7/0827

See application file for complete search history.

(56) References Cited

U.S. PATENT DOCUMENTS

| | | | | |
|---|---|---|---|---|
| 4,882,206 | A | 11/1989 | Erbil | |
| 5,012,022 | A | 4/1991 | Venier | |
| 6,175,027 | B1 | 1/2001 | Sullivan | |
| 6,939,928 | B1 * | 9/2005 | Kawai | C08F 10/00 526/170 |
| 7,579,415 | B2 | 8/2009 | Agapiou et al. | |
| 7,834,228 | B1 | 11/2010 | Voll Barclay | |
| 8,975,427 | B2 | 3/2015 | Harlan | |
| 2001/0047120 | A1 | 11/2001 | Kitada | |
| 2013/0085289 | A1 | 4/2013 | Harlan | |
| 2018/0166276 | A1 | 6/2018 | Nakao | |

FOREIGN PATENT DOCUMENTS

| | | | |
|---|---|---|---|
| CN | 103641676 | A | 3/2014 |
| JP | S5859929 | A | 4/1983 |
| JP | 2004285028 | A | 10/2004 |
| JP | 2007246513 | A | 9/2007 |
| JP | 2011178726 | A | 9/2011 |
| JP | 2012176915 | A | 9/2012 |
| JP | 2012211093 | A | 11/2012 |
| WO | 2013027958 | A1 | 2/2013 |
| WO | 2016171807 | A1 | 10/2016 |

OTHER PUBLICATIONS

Ito ("Product Class 10: Fulvenes" Science of Synthesis, Source: Fulvenes. Tobe Y, Siegel J, ed. Stuttgart: Thieme; 2010. doi: 10.1055/sos-SD-045-00354) (Year: 2010).*

Walter ("Spin Equilibria in Monomeric Manganocenes: Solid-State Magnetic and EXAFS Studies" Organometallics, 2009, p. 2005) (Year: 2009).*

Levet, Gaspard et al., Preparation of a Key Tetraene Precursor for the Synthesis of Long Acenes, Eur. J. Org. Chem. 2020, 1658-1664 (https://chemistry-europe.onlinelibrary.wiley.com/doi/10.1002/ejoc.201901868).

Paradies, Jan et al., Frustrated Lewis pair catalyzed hydrosilylation and hydrosilane mediated hydrogenation of fulvenes, Org. Biomol. Chem., 2014, 12, 9139.

Perevozchikova et al., Dihydrides of bis-isopropylcyclopentadienyl-tungsten and -molybdenum, Khimiya Elementoorganicheskikh Soedinenii (1976), 4, 95-7.

Stone, Keith J. et al., An exceptionally simple and efficient method for the preparation of a wide variety of fulvenes, J. Org. Chem. 1984, 49, 11, 1849-1853 (https://doi.org/10.1021/jo00185a001).

Walter, Marc D. et al., Spin Equilibria in Monomeric Manganocenes: Solid-State Magnetic and EXAFS Studies, Organometallics, 2009, 28, 7, 2005-2019, DOI: 10.1021/om800922j.

Westerhausen et al., Substituted Cyclopentadienides of Magnesium from the Reaction of Dialkyl Magnesium with Fulvenes., European Journal of Inorganic Chemistry., pp. 965-971., 1998.

(Continued)

*Primary Examiner* — Amy C Bonaparte

(57) ABSTRACT

The disclosure provides methodology for the synthesis of mono-alkylated cyclopentadiene structures, which can be obtained via fulvene intermediates. In one embodiment, the cyclopentadiene ring is substituted with a trialkylsilyl moiety, which enables the further reaction with certain metal halides to form metal adducts. For example, the monoalkyl cyclopentadienes substituted with a trimethylsilyl group can be reacted with $TiCl_4$ to provide $R^*CpTiCl_3$ complexes, wherein R* is a group of the formula

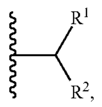

wherein $R^1$ and $R^2$ are as defined herein.

8 Claims, No Drawings

(56) References Cited

OTHER PUBLICATIONS

Wang, Yan et al., Ethylene-bridged C1-symmetric ansa-(3-R-indenyl)(fluorenyl) zirconocene complexes for propylene dimerization or polymerization: The effect of R group, Polyhedron, 76, 2014, 81-93.
Bitterwolf et al., Improved synthesis of (η5-CpR)M(CO)4 compounds and the Nujol matrix photochemistry of (η-C5H5)M(CO)4 and (η5-C9H7)M(CO)4, where M = Nb and Ta., Journal of Organometallic Chemistry., vol. 557., No. 1., pp. 77-92., 1998.
Chemical Abstract compound, STNext RN 343272-38-8 (Entered STN: Jun. 25, 2001).
Cheng et al., C—C and C-X coupling reactions of unactivated alkyl electrophiles using copper catalysis., Chemical Society Reviews., vol. 49 No. 22., pp. 8036-8064., 2020.
Nomura et al., Olefin Polymerization by (Cyclopentadienyl) (aryloxy) titanium (IV) Complexes-Cocatalyst Systems., 4 Macromolecules., vol. 31., No. 22., pp. 7588-7597., 1998.

* cited by examiner

MONOALKYL CYCLOPENTADIENE COMPOUNDS AND PROCESSES FOR PREPARING SAME

CROSS-REFERENCE TO RELATED APPLICATIONS

This application is a divisional application of U.S. patent application Ser. No. 17/988,544, filed Nov. 16, 2022, which claims the benefit under 35 USC § 119 of U.S. Provisional Patent Application No. 63/283,855, filed Nov. 29, 2021, the disclosures of which are incorporated herein by reference.

TECHNICAL FIELD

The present disclosure generally relates to a process for preparing mono-alkylated cyclopentadiene compounds.

BACKGROUND

Cyclopentadienes are useful as intermediates to many other useful organic compounds. Certain alkyl-substituted cyclopentadienes are useful as synthetic lubricants. (See, for example, U.S. Pat. Nos. 5,144,095 and 5,012,022. Additionally, the cyclopentadiene structure can also be found in many of the so-called single site metallocene catalysts used to make polyolefins such as polyethylenes and polypropylenes. (See, for example, U.S. Pat. No. 7,579,415).

One inherent difficulty in the handling of cyclopentadiene is that it tends to dimerize via a Diels-Alder reaction. This dimerization proceeds at room temperature over a period of hours, but can be reversed by utilization of heating, which in some cases requires a cracking procedure. Additionally, in alkylation reactions utilizing a cyclopentadiene anion species, the formation of di- and tri-alkyl species can be encountered, which further complicates the synthetic regime by reducing yields and necessitating further separation and purification.

Thus, a need exists for improved methodology for the mono-alkylation of cyclopentadiene structures.

SUMMARY

In summary, the disclosure provides methodology for the selective synthesis of mono-alkylated cyclopentadiene structures, which can be obtained via fulvene intermediates. In one embodiment, the cyclopentadiene ring is substituted with a trialkylsilyl moiety, which enables the further reaction with certain metal halides to form metal complexes. For example, the monoalkyl cyclopentadienes substituted with a trimethylsilyl group can be reacted with $TiCl_4$ to provide $R^*CpTiCl_3$ complexes, wherein R* is a group of the formula

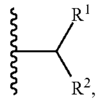

wherein $R^1$ and $R^2$ are as defined below. In this highly-selective process, the resulting products are mono-alkylated, with no dialkylation products detectible via gas chromatography or NMR. In this regard, the process of the disclosure is particularly useful for preparing (mono)isopropyl-substituted cyclopentadiene.

DETAILED DESCRIPTION

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The term "about" generally refers to a range of numbers that is considered equivalent to the recited value (e.g., having the same function or result). In many instances, the term "about" may include numbers that are rounded to the nearest significant figure.

Numerical ranges expressed using endpoints include all numbers subsumed within that range (e.g., 1 to 5 includes 1, 1.5, 2, 2.75, 3, 3.80, 4 and 5).

In one aspect, the disclosure provides a process for preparing a compound of the Formula (I):

(I)

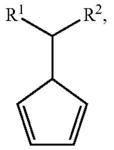

wherein $R^1$ and $R^2$ are independently chosen from hydrogen and $C_1$-$C_8$ alkyl, which comprises contacting a compound of the formula

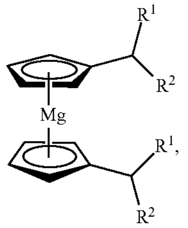

with a protic reagent.

In one embodiment of this aspect, the protic reagent is water, optionally containing an acid such as HCl (hydrochloric acid). In another embodiment, the protic reagent is an alcohol or polyol, optionally containing an acid. In another embodiment, $R^1$ and $R^2$ are methyl. In another embodiment, the alcohol is chosen from a $C_1$-$C_8$ alcohol.

In another aspect, the disclosure provides a process for preparing a compound of the Formula (I):

(I)

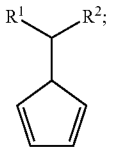

wherein $R^1$ and $R^2$ are independently chosen from hydrogen and $C_1$-$C_8$ alkyl;

which comprises contacting cyclopentadiene with a compound of the formula

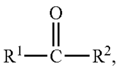

in the presence of a base, thereby forming a compound of the formula

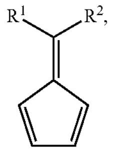

which is in turn treated with a dialkyl magnesium compound, thereby forming a compound of the formula

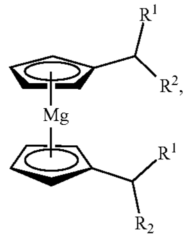

which is in turn treated with a protic reagent to provide a compound of Formula (I).

In general, the starting material fulvenes can be prepared by reacting cyclopentadiene with a ketone or aldehyde of the formula $R^1$—C(O)—$R^2$ in the presence of a base such as pyrrolidone or an alkali metal hydroxide. The magnesocene (2), shown in Scheme 1, is then formed by the reaction of the fulvene intermediate (1) with a dialkyl magnesium compound such as $Mg(CH_2CH_2CH_2CH_3)_2$, in a non-coordinating solvent such as hexanes. In this regard, suitable dialkyl magnesium compounds include compounds having alkyl groups capable of β-hydride elimination; examples include $Mg(C_2\text{-}C_8\ alkyl)_2$, $Mg(C_3\text{-}C_8\ alkyl)_2$, or $Mg(C_4\text{-}C_8\ alkyl)_2$. Scheme 1 below outlines the general synthetic scheme for quenching the magnesocene (2) with either a protic reagent or a trialkylsilyl halide (such as trimethylsilyl chloride) to provide the desired compounds:

Scheme 1: General synthetic scheme for the preparation of monoalkyl-cyclopentadienes

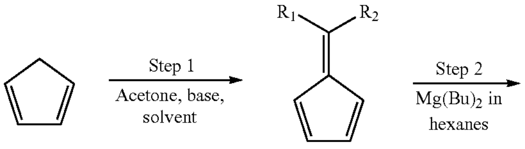

1

-continued

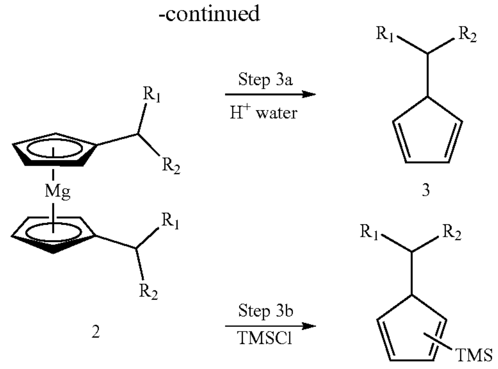

2

3

4

Accordingly, in a further aspect, the disclosure provides a process for preparing a compound of the Formula (II):

(II)

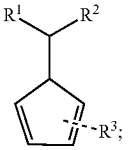

wherein $R^1$ and $R^2$ are independently chosen from hydrogen and $C_1$-$C_8$ alkyl; and $R^3$ is a group of the formula $(C_1\text{-}C_4\ alkyl)_3Si$—, which comprises contacting cyclopentadiene with a compound of the formula

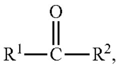

in a presence of a base, thereby forming a compound of the formula

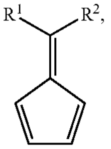

which is in turn treated with a dialkyl magnesium compound, thereby forming a compound of the formula

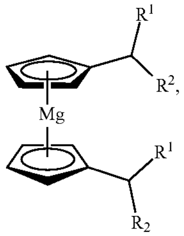

which is in turn treated with a compound of the formula $(C_1\text{-}C_4\ alkyl)_3Si$—X, wherein X is halo to provide a compound of the Formula (II).

In certain embodiments, $R^1$ and $R^2$ are chosen from hydrogen, methyl, ethyl, n-propyl, isopropyl, n-butyl, isobutyl, sec-butyl, n-pentyl, isopentyl, sec-pentyl, n-hexyl, isohexyl, sec-hexyl, n-heptyl, isoheptyl, sec-heptyl, n-octyl, isooctyl, and sec-octyl. In one embodiment, each of $R^1$ and $R^2$ is methyl. In one embodiment, $R^3$ is trimethylsilyl. In one embodiment, X is chosen from chloro, bromo, or iodo; in another embodiment, X is chloro.

The compounds of Formula (I) and Formula (II) are useful as intermediates in the synthesis of metallocene catalysts. Additionally, the compounds of Formula (II) are useful in the preparation of Group IV, Group V, and Group VI and metal-substituted compounds in the plus four oxidation state, via reaction with the corresponding metal halides. For example, the compound of the Formula (II), wherein $R^3$ is trimethylsilyl, can be reacted with $TiCl_4$ to provide a $R^*CpTiCl_3$ complex.

In the disclosure, the processes which begin with a substituted fulvene starting material thus enable the synthesis of exclusively monoalkyl-substituted compounds versus formation of multi-alkylated cyclopentadienyl species, which can occur in ordinary alkylation reaction approaches where the product can become deprotonated by the initial metal-Cp complex (i.e., anionic cyclopentadiene) prior to a second alkylation with, for example alkyl bromide. In the latter case, levels of multi-alkylation can range from 0.5-5 weight percent. Advantageously, the processes of the disclosure provide mono-alkylated species with no detectible levels of multi-alkylated species by gas chromatography (e.g., GC and GC-MS) or NMR. Thus, in a further embodiment, the processes of the disclosure provide products having less than 0.5 weight percent, less than 0.3, or less than 0.1 weight percent of multi-alkylated species, as determined by gas chromatography.

Additionally, given the substituted fulvene approach outlined herein, the disclosure further advantageously provides the products of Formula (I) and (II), devoid of dicyclopentadiene and mixed dicyclopentadiene species.

The compounds of Formula (I) and (II), i.e., monoalkyl-substituted cyclopentadienes, are also useful as intermediates in the synthesis of metallocene catalysts, useful in the synthesis of various polyolefins, or alternatively as intermediates for precursors useful in atomic layer deposition (ALD) and chemical vapor deposition (CVD).

EXAMPLES

Synthetic Procedure for the Preparation $^i$PrCp and $^i$PrCp-TMS

Step 1: Synthesis of 6,6-dimethylfulyene (1e)

Acetone (1000 g, 17.2 mol), methanol (3 L, 2360 g), and cyclopentadiene ("Cp") (1138 g. 17.2 mmol) were added to flask. The resulting mixture was cooled to −10° C. Pyrrolidine (100 g, 1.4 mol) was added in portions while maintaining <0° C. temperatures. After pyrrolidine addition completion, the resulting mixture was stirred for 2 hours at −10° C. to 0° C. The reaction mixture was warmed to room temperature and stirred overnight. The resulting mixture cooled to 0-5° C., and an aqueous 4% acetic acid solution (3000 mL) was added. The resulting biphasic mixture was settled, and the aqueous layer discarded. The organic phase was washed with brine, and the residual solvents were removed with vacuum. 6,6-Dimethylfulyene (1740 g) was obtained in 95% yield and 96% purity by $^1$H-NMR and GC. Further purification by distillation resulted in 90% yield and 99% purity by $^1$H-NMR and GC.

Compounds 1 a-f were prepared with the same procedure with appropriate aldehydes/ketones.

Step 2: Synthesis of bis[1-isopropyl-2,4-cyclopentadiene-1-yl] Magnesium (2e)

6,6-Dimethylfulvene (21.2 g, 0.2 mol) and hexanes (50 mL) were added to a flask under nitrogen. 1M di-n-Butylmagnesium in heptanes (100 mL, 0.1 mol) was added dropwise while maintaining <50° C. temperatures. After the addition of di-n-butylmagnesium, the resulting solution stirred at room temperature overnight. Complete removal of volatiles under vacuum produced bis[1-isopropyl-2,4-cyclopentadiene-1-yl]magnesium (23.2 g) in 98.3% yield and 99% purity by $^1$H-NMR.

Note: n-butyl-sec-butylmagnesium in hexanes can be used instead di-n-butylmagnesium heptanes.

Compounds 2a, 2c, 2e and 2f were prepared with the same procedure with appropriate fulvenes.

Step 3A: Synthesis of isopropyl-Cp (3e)

Bis[1-isopropyl-2,4-cyclopentadiene-1-yl] magnesium (10 g) and hexanes (100 mL) were added into a flask under nitrogen. The resulting mixture was cooled to 0° C., and 0.1 M FICA (25 mL) was added dropwise while maintaining <5° C. temperatures. The resulting mixture was warmed to room temperature. The aqueous layer discarded, and the organic layer dried with anhydrous magnesium sulfate. The resulting mixture filtered, Hexanes removal under reduced pressure produced isopropyl cyclopentadiene (8.3 g, mixture of isomers) in 91% yield and 98% purity by $^1$H-NMR and GC.

Note: Water, alcohols can he used instead of 0.1 M HCl solution.

Compounds 3a, 3c, 3e and 3f were prepared with the same procedure with appropriate bis(cyclopentadienyl)magnesium complexes.

Step 3B: Synthesis of isopropyltrimethylsilyl-Cp (4e)

Bis[1-isopropyl-2,4-cyclopentadiene-1-yl] magnesium (10 g) and hexanes (100 mL) were added into a flask under nitrogen. The resulting mixture was cooled to 0° C., and trimethylsilyl chloride (9.3 g) added dropwise while maintaining <5° C. temperatures. The resulting mixture was warmed to room temperature and passed through a silica plug. Hexanes removal under reduced pressure produced isopropyltrimethylsilylcyclopentadiene (13.8 g, mixture of isomers) in 90% yield and 98% purity by $^1$H-NMR.

Compounds 4c, 4e and 4f were prepared with the same procedure with appropriate bis(cyclopentadienyl)magnesium complexes.

TABLE 1

Summary of alkyl-Cps and alkyl-Cp-TMS materials

| Compound | Aldehyde/ Ketone | Fulvene Yield % | $RCp_2Mg$ Yield % | RCp yield % [NMR yield] | RCp Purity [$^1$H-NMR] |
|---|---|---|---|---|---|
| EthylCp | Acetaldehyde | 40% (1a) | 90% (2a) | 75% (3 a) | 40% EtCp, 35% EtCp dimer |

TABLE 1-continued

Summary of alkyl-Cps and alkyl-Cp-TMS materials

| Compound | Aldehyde/ Ketone | Fulvene Yield % | $RCp_2Mg$ Yield % | RCp yield % [NMR yield] | RCp Purity [$^1$H-NMR] |
|---|---|---|---|---|---|
| PropylCp | Propanal | 52% (1b) | — | — | — |
| ButylCp | Butanal | 80% (1c) | 98% (2c) | 84% (3 c) | 97% |
| PentylCp | Pentanal | 62% (1d) | — | — | — |
| isopropylCp | Acetone | 90% (1e) | 98% (2e) | 90% (3e) | 98% |
| sec-butylCp | sec-butanal | 83% (1f) | 98% (2f) | 82% (3f) | 99% |
| EthylCpTMS | Acetaldehyde | 40% (1a) | 90% (2a) | — | — |
| PropylCpTMS | Propanal | 52% (1b) | — | — | — |
| ButylCpTMS | Butanal | 80% (1c) | 98% (2c) | 84% (4c) | 97% |
| PentylCpTMS | Pentanal | 62% (1d) | — | — | — |
| isopropyl-CpTMS | Acetone | 90% (1e) | 98% (2e) | 90% (4e) | 98% |
| sec-butyl-CpTMS | sec-butanal | 83% (1f) | 98% (2f) | 82% (4f) | 99% |

Aspects

In a first aspect, the disclosure provides a process for preparing a compound of the Formula (I):

(I)

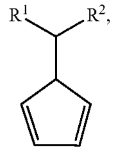

wherein $R^1$ and $R^2$ are independently chosen from hydrogen and $C_1$-$C_8$ alkyl, which comprises contacting a compound of the formula

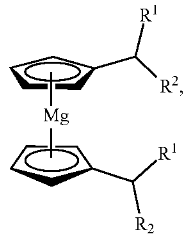

with a protic reagent.

In a second aspect, the disclosure provides the process of the first aspect, wherein the protic reagent is water.

In a third aspect, the disclosure provides the process of the second aspect, wherein the water further comprises an acid.

In a fourth aspect, the disclosure provides the process of the first aspect, wherein the protic reagent is an alcohol or polyol.

In a fifth aspect, the disclosure provides the process of the fourth aspect, wherein the protic reagent further comprises an acid.

In a sixth aspect, the disclosure provides the process of any one of the first through the fifth aspects, wherein $R^1$ and $R^2$ are methyl.

In a seventh aspect, the disclosure provides the process of the fourth aspect, wherein the alcohol is chosen from a $C_1$-$C_8$ alcohol.

In an eighth aspect, the disclosure provides the process of any one of the first through the seventh aspects, wherein the compound of Formula (I) has less than about 0.5 weight percent, less than about 0.3 weight percent, or less than about 0.1 weight percent, of multi-alkylated species, as determined by gas chromatography.

In a ninth aspect, the disclosure provides the process of any one of the first through eighth aspects, wherein the compound of Formula (I) is devoid of dicyclopentadiene and mixed dicyclopentadiene species.

In a tenth aspect, the disclosure provides a process for preparing a compound of the Formula (I):

(I)

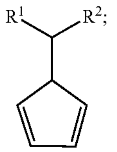

wherein $R^1$ and $R^2$ are independently chosen from hydrogen and $C_1$-$C_8$ alkyl, which comprises contacting cyclopentadiene with a compound of the formula

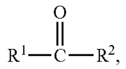

in the presence of a base, thereby forming a compound of the formula

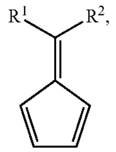

which is in turn treated with a dialkyl magnesium compound, thereby forming a compound of the formula

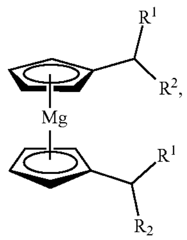

which is in turn treated with a protic reagent to provide a compound of Formula (I).

In an eleventh aspect, the disclosure provides the process of the tenth aspect, wherein the protic reagent is water.

In a twelfth aspect, the disclosure provides the process of the eleventh aspect, wherein the water further comprises an acid.

In a thirteenth aspect, the disclosure provides the process of the tenth aspect, wherein the protic reagent is an alcohol or polyol.

In a fourteenth aspect, the disclosure provides the process of the thirteenth aspect, wherein the alcohol or polyol further comprises an acid.

In a fifteenth aspect, the disclosure provides the process of any one of the tenth through fourteenth aspects, wherein $R^1$ and $R^2$ are methyl.

In a sixteenth aspect, the disclosure provides the process of the thirteenth or fourteenth aspects, wherein the alcohol is chosen from a $C_1$-$C_8$ alcohol.

In a seventeenth aspect, the disclosure provides a process for preparing a compound of the Formula (II):

(II)

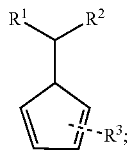

wherein $R^1$ and $R^2$ are independently chosen from hydrogen and $C_1$-$C_8$ alkyl; and $R^3$ is a group of the formula $(C_1$-$C_4$ alkyl$)_3$Si—, which comprises contacting cyclopentadiene with a compound of the formula

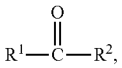

thereby forming a compound of the formula

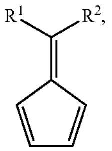

which is in turn treated with a dialkyl magnesium compound, thereby forming a compound of the formula

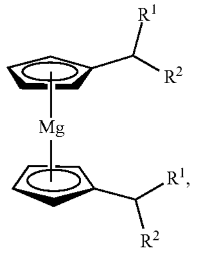

which is in turn treated with a compound of the formula $(C_1$-$C_4$ alkyl$)_3$Si—X, wherein X is halo to provide a compound of the Formula (II).

In an eighteenth aspect, the disclosure provides the process of the seventeenth aspect, wherein each of $R^1$ and $R^2$ is methyl.

In a nineteenth aspect, the disclosure provides the process of the seventeenth or eighteenth aspects, wherein $R^3$ is trimethylsilyl.

In a twentieth aspect, the disclosure provides the process of the seventeenth, eighteenth, or nineteenth aspects, wherein X is chloro.

In a twenty-first aspect, the disclosure provides the process of any one of the seventeenth through the twentieth aspects, wherein the compound of Formula (II) has less than about 0.5 weight percent, less than about 0.3 weight percent, or less than about 0.1 weight percent, of multi-alkylated species, as determined by gas chromatography.

In a twenty-second aspect, the disclosure provides the process of any one of the seventeenth through the twenty-first aspects, wherein the compound of Formula (II) is devoid of dicyclopentadiene and mixed dicyclopentadiene species.

In a twenty-third aspect, the disclosure provides the process of any one the seventeenth through the twenty-second aspects, further comprising the step of treating the compound of Formula (II) with a Group IV, Group V, or Group VI metal halide.

In a twenty-fourth aspect, the disclosure provides the process of the twenty-third aspect, wherein the metal halide is $TiCl_4$.

In a twenty-fifth aspect, the disclosure provides a compound of Formula (I):

(I)

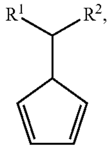

wherein $R^1$ and $R^2$ are independently chosen from hydrogen and $C_1$-$C_8$ alkyl, and wherein the compound of Formula (I) has less than about 0.5 weight percent of multi-alkylated species, as determined by gas chromatography.

In a twenty-sixth aspect, the disclosure provides the compound of the twenty-fifth aspect, wherein $R^1$ and $R^2$ are methyl.

In a twenty-seventh aspect, the disclosure provides the compound of twenty-fifth or twenty-sixth aspect, wherein the compound of Formula (I) is devoid of dicyclopentadiene and mixed dicyclopentadiene species.

In a twenty-eighth aspect, the disclosure provides a compound of Formula (I), as claimed in any of the twenty-fifth through twenty-seventh aspects, wherein the compound of Formula (I) has less than about 0.3 weight percent of multi-alkylated species, as determined by gas chromatography.

In a twenty-ninth aspect, the disclosure provides a compound of Formula (I), as claimed in any of the twenty-fifth through twenty-seventh aspects, wherein the compound of Formula (I) has less than about 0.1 weight percent of multi-alkylated species, as determined by gas chromatography.

In a thirtieth aspect, the disclosure provides a compound of Formula (II):

(II)

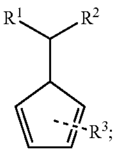

wherein $R^1$ and $R^2$ are independently chosen from hydrogen and $C_1$-$C_8$ alkyl; and $R^3$ is a group of the formula ($C_1$-$C_4$ alkyl)$_3$Si—, wherein the compound of Formula (II) has less than about 0.5 weight percent of multi-alkylated species, as determined by gas chromatography.

In a thirty-first aspect, the disclosure provides the compound of the thirtieth aspect, wherein $R^1$ and $R^2$ are methyl.

In a thirty-second aspect, the disclosure provides the compound of the thirtieth or thirty-first aspect, wherein the compound of Formula (II) is devoid of dicyclopentadiene and mixed dicyclopentadiene species.

In a thirty-third aspect, the disclosure provides a compound of Formula (II), as claimed in any of the thirtieth through thirty-second aspects, wherein the compound of Formula (II) has less than about 0.3 weight percent of multi-alkylated species, as determined by gas chromatography.

In a thirty-fourth aspect, the disclosure provides a compound of Formula (II), as claimed in any of the thirtieth through thirty-second aspects, wherein the compound of Formula (II) has less than about 0.1 weight percent of multi-alkylated species, as determined by gas chromatography.

Having thus described several illustrative embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respects, only illustrative. The disclosure's scope is, of course, defined in the language in which the appended claims are expressed.

What is claimed is:

1. A process for preparing a compound of the Formula (II):

(II)

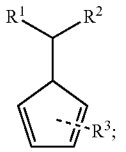

wherein $R^1$ and $R^2$ are independently chosen from hydrogen and $C_1$-$C_8$ alkyl; and $R^3$ is a group of the formula ($C_1$-$C_4$ alkyl)$_3$Si—, the process comprising:

contacting cyclopentadiene with a compound of the formula

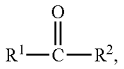

thereby forming a compound of the formula

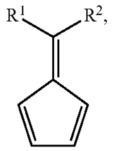

which is in turn treated with a dialkyl magnesium compound, thereby forming a compound of the formula

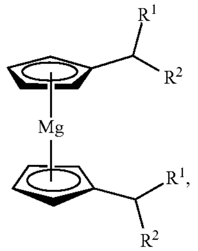

which is in turn treated with a compound of the formula ($C_1$-$C_4$ alkyl)$_3$Si—X, wherein X is halo to provide a compound of the Formula (II).

2. The process of claim 1, wherein each of $R^1$ and $R^2$ is methyl.

3. The process of claim 1, wherein $R^3$ is trimethylsilyl.

4. The process of claim 1, wherein X is chloro.

5. The process of claim 1, wherein the compound of Formula (II) has less than about 0.5 weight percent of multi-alkylated species, as determined by gas chromatography.

6. The process of claim 1, wherein the compound of Formula (II) is devoid of dicyclopentadiene and mixed dicyclopentadiene species.

7. The process of claim 1, further comprising the step of treating the compound of Formula (II) with a Group IV, Group V, or Group VI metal halide.

8. The process of claim 7, wherein the metal halide is $TiCl_4$.

* * * * *